(12) United States Patent
Wagner et al.

(10) Patent No.: US 10,221,143 B2
(45) Date of Patent: Mar. 5, 2019

(54) SUBSTITUTED ANILINES FOR TREATMENT OF ANIMAL DISEASES

(71) Applicant: ARIZONA BOARD OF REGENTS ON BEHALF OF ARIZONA STATE UNIVERSITY, Scottsdale, AZ (US)

(72) Inventors: Carl Wagner, Scottsdale, AZ (US); Peter Jurutka, Scottsdale, AZ (US); Pamela Marshall, Scottsdale, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 15/550,259

(22) PCT Filed: Mar. 1, 2016

(86) PCT No.: PCT/US2016/020283
§ 371 (c)(1),
(2) Date: Aug. 10, 2017

(87) PCT Pub. No.: WO2016/140978
PCT Pub. Date: Sep. 9, 2016

(65) Prior Publication Data
US 2018/0065936 A1 Mar. 8, 2018

Related U.S. Application Data

(60) Provisional application No. 62/127,724, filed on Mar. 3, 2015.

(51) Int. Cl.
| | | |
|---|---|---|
| *A61K 31/136* | (2006.01) | |
| *C07C 211/48* | (2006.01) | |
| *C07D 239/42* | (2006.01) | |
| *C07D 213/79* | (2006.01) | |
| *C07D 237/24* | (2006.01) | |
| *C07D 241/28* | (2006.01) | |
| *C07C 229/60* | (2006.01) | |
| *C07D 213/80* | (2006.01) | |

(52) U.S. Cl.
CPC .......... *C07D 239/42* (2013.01); *C07C 229/60* (2013.01); *C07D 213/79* (2013.01); *C07D 213/80* (2013.01); *C07D 237/24* (2013.01); *C07D 241/28* (2013.01); *C07C 2601/02* (2017.05)

(58) Field of Classification Search
CPC ............................. A61K 31/136; C07C 211/48
USPC ........................................... 514/649; 564/305
See application file for complete search history.

(56) References Cited

U.S. PATENT DOCUMENTS

| | | | |
|---|---|---|---|
| 4,826,984 A | 5/1989 | Berlin et al. | |
| 4,938,949 A | 7/1990 | Borch et al. | |
| 5,006,550 A | 4/1991 | Chandraratna | |
| 5,414,156 A | 5/1995 | Cho et al. | |
| 5,672,710 A | 9/1997 | Beard et al. | |
| 6,172,112 B1 | 1/2001 | Brouillette et al. | |
| 6,596,758 B1 | 7/2003 | Brunet et al. | |
| 9,174,917 B2 | 11/2015 | Wagner et al. | |
| 2010/0120742 A1* | 5/2010 | Kakuta ............... A61K 31/4409 | 514/211.09 |
| 2014/0343079 A1 | 11/2014 | Wagner et al. | |

FOREIGN PATENT DOCUMENTS

| | | |
|---|---|---|
| JP | 2013052386 A | 3/2013 |
| JP | 2014076953 A | 5/2014 |
| JP | 5784045 B2 | 10/2017 |
| WO | 2008105386 A1 | 9/2008 |
| WO | 2011103321 A1 | 8/2011 |
| WO | 2015109318 A2 | 7/2015 |
| WO | 2015130973 A1 | 9/2015 |
| WO | 2016140979 A1 | 9/2016 |

OTHER PUBLICATIONS

Atigadda, et al., "Methyl substitution of a rexinoid agonist improves potency and reveals site of lipid toxicity", Journal of Medicinal Chemistry 57(12), 5370-5380 (2014).
Batie, et al., "Synthesis and biological evaluation of halogenated curcumin analogs as potential nuclear receptor selective agonists", Bioorganic Med Chem 21(3), 693-702 (2013, epub 2012).
Cesario, et al., "Differentiation and growth inhibition mediated via the RXR:PPARgamma heterodimer in colon cancer", Cancer Letters 240(2), 225-233 (2006).
Esteva, et al., "Multicenter Phase II Study of Oral Bexarotene for Patients With Metastatic Breast Cancer", Journal of Clinical Oncology 21(6), 999-1006 (2003).
Fantini, et al., "Bexarotene blocks calcium-permeable ion channels formed by neurotoxic Alzheimer's β-amyloid peptides.", ACS Chemical Neuroscience 5, 216-224 (2014).
Fujii, et al., "Effect of retinoid X receptor partial agonist on airway inflammation and hyperresponsiveness", Eur Respir J 46(suppl. 59), PA4007 (2015).
Furmick, et al., "Modeling, synthesis and biological evaluation of potential retinoid X receptor-selective agonists: novel halogenated analogues of 4-[1-(3,5,5,8,8-pentamethyl-5,6,7,8-tetrahydro-2-naphthyl)ethynyl]benzoic acid (bexarotene)", ChemMedChem 7(9), 1551-1566 (2012).
Heck, et al., "Modeling, Synthesis, and Biological Evaluation of Potential Retinoid X Receptor (RXR)-Selective Agonists: Analogues of 4-[1-(3,5,5,8,8-Pentamethyl-5,6,7,8-tetrahydro-2-naphthyl)ethynyl]benzoic Acid (Bexarotene) and 6-(Ethyl(5,5,8,8-tetrahydronaphthalen-2-y", J Med Chem 59(19), 8924-8940 (2016).

(Continued)

*Primary Examiner* — Douglas M Willis
(74) *Attorney, Agent, or Firm* — Viksnins Harris Padys Malen LLP

(57) ABSTRACT

The invention provides alkyl benzene compounds. The compounds are useful for treating conditions including Alzheimer's disease, Parkinson's disease, diabetes, cancer, inflammation, hyperresponsiveness, allergic conditions, asthma, and psychotic disorders such as schizophrenia. The compounds are also useful to lower IL-4, IL-5, or IL-15 levels in an animal.

9 Claims, No Drawings

(56) References Cited

OTHER PUBLICATIONS

Jurutka, et al., "Modeling, synthesis, and biological evaluation of potential retinoid X receptor (RXR) selective agonists: novel analogues of 4[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).

Kakuta, "Western-style Chinese (Kampo) medicine targeting retinoid X receptors (RXRs)", 248th ACS National Meeting, MEDI 102, San Francisco, CA. (2014).

Kawata, et al., "RXR partial agonist produced by side chain repositioning of alkoxy RXR full agonist retains antitype 2 diabetes activity without the adverse effects", J Med Chem 58(2), 912-926 (2015, epub 2014).

Khuri, et al., "Multi-Institutional Phase I/II Trial of Oral Bexarotene in Combination With Cisplatin and Vinorelbine in Previously Untreated Patients With Advanced Non-Small-Cell Lung Cancer", Journal of Clinical Oncology 19, 2626-2637 (2001).

Kobayashi, et al., "Positron emission tomography to elucidate pharmacokinetic differences of regioisomeric retinoid x receptor agonists", ACS Med Chem Lett 6(3), 334-338 (2015).

Lerner, et al., "Bexarotene as add-on to antipsychotic treatment in schizophrenia patients: a pilot open-label trial.", Clinical Neuropharmacology 31(1), 25-33 (2008).

Liby, et al., "Synthetic Triterpenoids Prolong Survival in a Transgenic Mouse Model of Pancreatic Cancer", Cancer Prevention Research 3(11), 1427-1434 (2010).

Marshall, et al., "Analysis of differential secondary effects of novel rexinoids: select rexinoid X receptor ligands demonstrate differentiated side effect profiles", Pharma Res Per 3(2), e00122 (2015).

McFarland, et al., "Low dose bexarotene treatment rescues dopamine neurons and restores behavioral function in models of Parkinson's disease", ACS Chemical Neuroscience 4, 1430-1438 (2013).

Mortelmens, et al., "The Ames *Salmonella*/microsome mutagenicity assay", Mutat Res 455(1-2), 29-60 (2000).

Mukherjee, et al., "Sensitization of diabetic and obese mice to insulin by retinoid X receptor agonists", Nature 386, 407-410 (1997).

Takamatsu, et al., "The first potent subtype-selective retinoid X receptor (RXR) agonist possessing a 3-isopropoxy-4-isopropylphenylamino moiety, NEt-3IP (RXRalpha/beta-dual agonist)", ChemMedChem 3(5), 780-787.

Okayama University, "Synthesis of novel homeostasis modulators by "Westernized Kampo Medicine"—Retinoid X Receptor Partial-Agonists Exert Anti-type 2 Diabetes Effects with Less Adverse Effects than Full-Agonists—", Okayama University eBulletin 7, pp. 20-21 (Jun. 2014).

Patent Cooperation Treaty, International Bureau, International Preliminary Report on Patentability for PCT/US2016/020283, 7 pages, dated Sep. 5, 2017.

Patent Cooperation Treaty, International Bureau, International Preliminary Report on Patentability for PCT/US2016/020285, 6 pages, dated Sep. 5, 2017.

Patent Cooperation Treaty, International Searching Authority, Search Report and Written Opinion for PCT/US16/20283, 10 pages, dated May 19, 2016.

Patent Cooperation Treaty, International Searching Authority, Search Report and Written Opinion for PCT/US16/20285, 8 pages, dated May 20, 2016.

PUBCHEM, CID-58901647, create date Aug. 19, 2012.

Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene)", J. Med. Chem. 52, 5950-5966 (2009).

Yen, et al., "A selective retinoid X receptor agonist bexarotene (Targretin) prevents and overcomes acquired paclitaxel (Taxol) resistance in human non-small cell lung cancer", Clinical Cancer Research 10(24), 8656-8664 (2004).

* cited by examiner

SUBSTITUTED ANILINES FOR TREATMENT OF ANIMAL DISEASES

PRIORITY OF INVENTION

This application claims priority from U.S. Provisional Patent Application No. 62/127,724, filed 3 Mar. 2015, which is hereby incorporated by reference in its entirety.

GOVERNMENT FUNDING

This invention was made with government support under R15 CA139364 awarded by the National Institutes of Health. The government has certain rights in the invention.

BACKGROUND OF THE INVENTION

The human retinoid X receptors (hRXRs) consist of three identified isoforms ($\alpha$, $\beta$, $\gamma$) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Bexarotene has been used to treat cutaneous T cell lymphoma. Bexarotene has also been shown to be useful for treatment of Alzheimer's Disease (AD). However, bexarotene treatment results in untoward side effects, possibly due to its nonspecific nature of binding RXR in several states, including the RXR-RXR homodimer form as well as RXR heterodimer forms.

McFarland, K., et al, *ACS Chem. Neurosci.*, 2013, 4(11), 1430-1438 treated a rat model of Parkinson's disease (PD) with bexarotene and noted marked improvement in the PD symptoms. Specifically the bexarotene restored dopamine cells and natural behavior in the PD model. As importantly, the bexarotene dose that accomplished this was quite low, alleviating some side effects. The researchers demonstrated that these symptoms were alleviated by bexarotene binding to RXR and its heterodimerizing with another nuclear receptor called Nurr1.

PD is a chronic, debilitating disorder in which the neurons of the central nervous system degenerate over time. Specifically the dopamine secreting cells of the midbrain slowly die off, leaving the patient with a wide range of symptoms due to the lack of dopamine. Early symptoms include shaking, off balance gait, and slowless of muscles. Over time, symptoms worsen and additional symptoms including dementia and/or depression can develop. Treatments include dopamine agonists, given to try to ameliorate the effect of loss of dopamine in the system.

The compounds Net-41B and 100 have been reported to be effective as a retinoid-X-receptor (RXR) agonist with reduced side effect profiles. Kakuta, H. "Western-style Chinese (Kampo) medicine targeting retinoic X receptors (RXRs)." 248th ACS National Meeting; San Francisco, Calif. 2014; and Kakuta, H. "Retinoid X receptor partial agonist and pharmaceutical agent containing the same" from Jpn. Kokai Tokkyo Koho (2014), JP 2014076953 A 20140501.

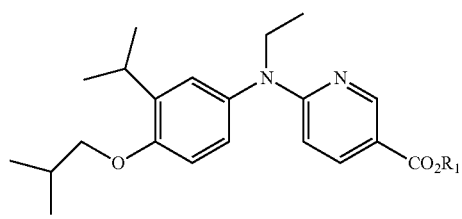

NEt-41B

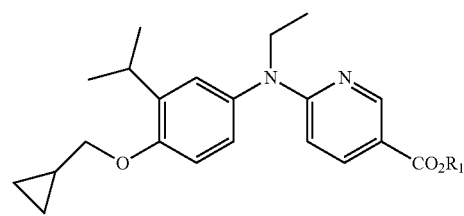

100

Additionally compound 101-104 have been reported to be effective as retinoid-X-receptor (RXR) agonists with potential as a therapeutic agent for treating for human cancers (Takamatsu, K., et al., *Chem Med Chem* 2008, 3, 780-787).

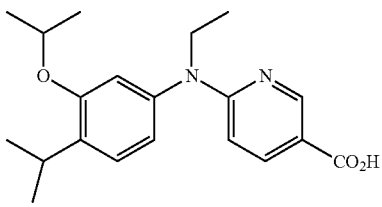

101

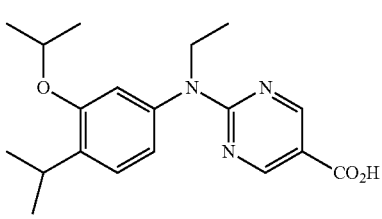

102

-continued

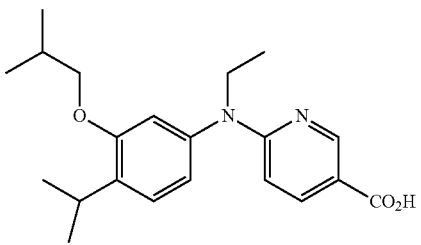

103

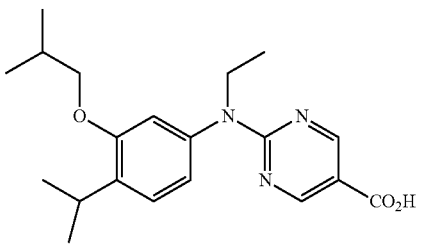

104

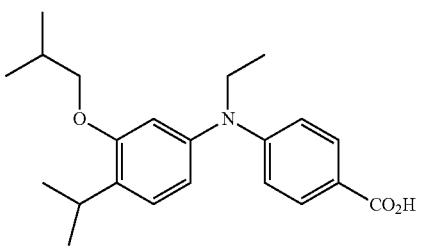

105

Compound 105 has also been reported.

Currently there is a need for additional chemical agents that are useful for treating conditions including Alzheimer's disease, Parkinson's disease, diabetes, cancer, and psychotic disorders such as schizophrenia.

SUMMARY OF THE INVENTION

The present invention provides compounds that are useful for treating conditions including Alzheimer's disease, Parkinson's disease, diabetes, cancer, and psychotic disorders such as schizophrenia.

Accordingly, one embodiment provides a compound of the invention which is compound of formula (I), or a salt thereof:

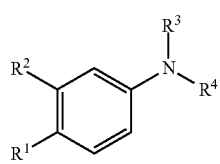

(I)

wherein:

$R^1$ is $(C_3-C_6)$alkyl, $(C_3-C_6)$cycloalkyl-$(C_1-C_3)$alkyl-, $(C_3-C_6)$alkoxy, or $(C_3-C_6)$cycloalkyl-$(C_1-C_3)$alkoxy-;

$R^2$ is $(C_3-C_6)$alkyl, $(C_3-C_6)$cycloalkyl-$(C_1-C_3)$alkyl-, $C_3-C_6$)alkoxy, or $(C_3-C_6)$cycloalkyl-$(C_1-C_3)$alkoxy-;

$R^3$ is $(C_1-C_6)$alkyl or $(C_3-C_6)$cycloalkyl-$(C_1-C_3)$alkyl-;

$R^4$ is a six-membered aromatic ring comprising carbon atoms and 0, 1, 2, or 3 nitrogen atoms, which ring is substituted at the position para to the point of attachment to the nitrogen in Formula (I) with a group —$CO_2R^c$ and which ring is optionally further substituted on a carbon atom with one or more groups independently selected from halo, hydroxy, nitro, cyano, —$NR^aR^b$, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, wherein each $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, —$NR^aR^b$, and oxo (=O);

$R^a$ and $R^b$ are each independently H or $(C_1-C_6)$alkyl; or $R^a$ and $R^b$ taken together with the nitrogen to which they are attached form a ring selected from aziridine, azetidino, pyrrolidino, and morpholino; and $R^c$ is H or $(C_1-C_6)$alkyl;

provided the compound of formula (I) is not:

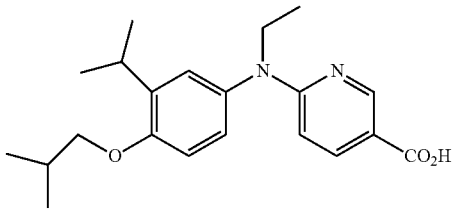

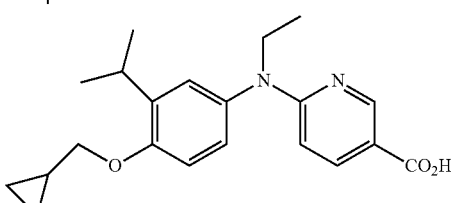

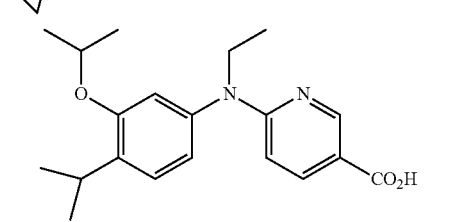

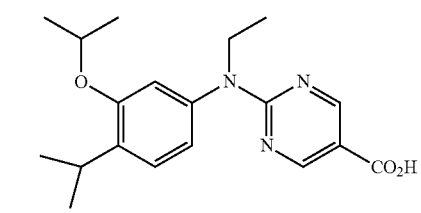

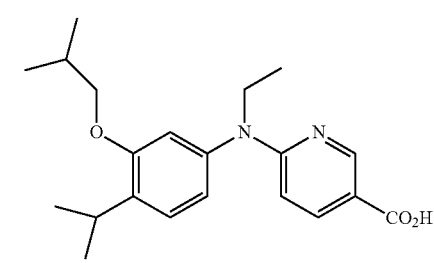

-continued

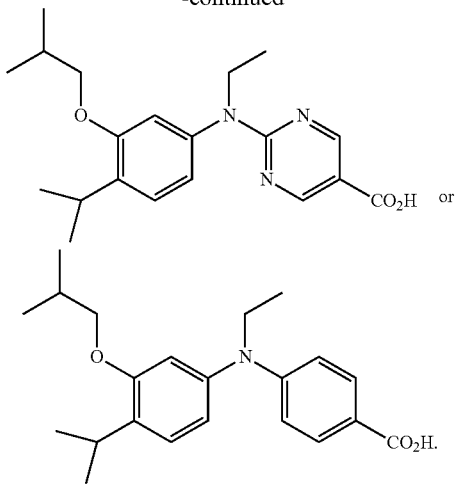

The invention also provides a pharmaceutical composition comprising a compound of formulae (I), or a pharmaceutically acceptable salt thereof, and a pharmaceutically acceptable diluent or carrier.

The invention also provides a method for treating Alzheimer's disease, Parkinson's disease, diabetes, cancer, or a psychotic disorder in an animal (e.g. a mammal such as a human) comprising administering to the animal a compound of formulae (I), or a pharmaceutically acceptable salt thereof.

The invention also provides a compound of formulae (I), or a pharmaceutically acceptable salt thereof, for the prophylactic or therapeutic treatment of Alzheimer's disease, Parkinson's disease, diabetes, cancer, or a psychotic disorder.

The invention also provides the use of a compound of formulae (I), or a pharmaceutically acceptable salt thereof, to prepare a medicament useful for treating Alzheimer's disease, Parkinson's disease, diabetes, cancer, or a psychotic disorder in an animal.

The invention also provides a method for activating RXR in a cell comprising contacting the cell in vitro or in vivo with an effective amount of a compound of formulae (I), or a salt thereof.

The invention also provides a compound of formulae (I), or a pharmaceutically acceptable salt thereof, for use in medical therapy.

The invention also provides a method to reduce inflammation or hyperresponsiveness in an animal comprising administering a compound as described in any one of claims 1-17 or a pharmaceutically acceptable salt thereof, to the animal.

The invention also provides a method to lower IL-4, IL-5, or IL-15 levels in an animal comprising administering a compound as described in any one of claims 1-17 or a pharmaceutically acceptable salt thereof, to the animal.

The invention also provides a method to treat an allergic condition in an animal comprising administering a compound as described in any one of claims 1-17 or a pharmaceutically acceptable salt thereof, to the animal.

The invention also provides a method to treat asthma in an animal comprising administering a compound as described in any one of claims 1-17 or a pharmaceutically acceptable salt thereof, to the animal.

The invention also provides a compound as described in any one of claims 1-17 or a pharmaceutically acceptable salt thereof, for the prophylactic or therapeutic treatment of inflammation or hyperresponsiveness.

The invention also provides a compound as described in any one of claims 1-17 or a pharmaceutically acceptable salt thereof, to lower IL-4, IL-5, or IL-15 levels in an animal.

The invention also provides a compound as described in any one of claims 1-17 or a pharmaceutically acceptable salt thereof, for the prophylactic or therapeutic treatment of an allergic condition.

The invention also provides a compound as described in any one of claims 1-17 or a pharmaceutically acceptable salt thereof, for the prophylactic or therapeutic treatment of asthma.

The invention also provides the use of a compound as described in any one of claims 1-17 or a pharmaceutically acceptable salt thereof, to prepare a medicament useful to reduce inflammation or hyperresponsiveness in an animal.

The invention also provides the use of a compound as described in any one of claims 1-17 or a pharmaceutically acceptable salt thereof, to prepare a medicament useful to lower IL-4, IL-5, or IL-15 levels in an animal.

The invention also provides the use of a compound as described in any one of claims 1-17 or a pharmaceutically acceptable salt thereof, to prepare a medicament useful to treat an allergic condition in an.

The invention also provides the use of a compound as described in any one of claims 1-17 or a pharmaceutically acceptable salt thereof, to prepare a medicament useful to treat asthma in an animal.

The invention also provides a method to treat diabetes (e.g. Type II diabetes) in an animal comprising administering a compound as described in any one of claims 1-17 or a pharmaceutically acceptable salt thereof, to the animal.

The invention also provides a compound as described in any one of claims 1-17 or a pharmaceutically acceptable salt thereof, for the prophylactic or therapeutic treatment of diabetes (e.g. Type II diabetes).

The invention also provides the use of a compound as described in any one of claims 1-17 or a pharmaceutically acceptable salt thereof, to prepare a medicament useful to treat diabetes (e.g. Type II diabetes) in an animal (e.g. a human).

The invention also provides a method to prepare the compound:

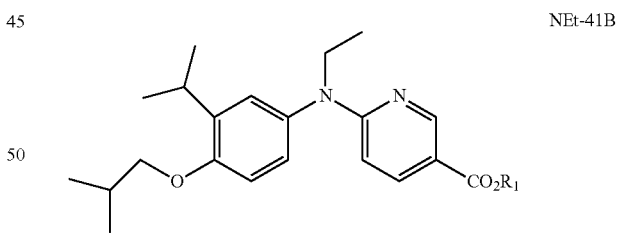

NEt-41B or a salt thereof that comprises a step of alkylating 2-isopropyl phenol to give 1-isobutoxy-2-isopropylbenzene.

The invention also provides a method to prepare 1-isobutoxy-2-isopropylbenzene comprising alkylating 2-isopropyl phenol to give 1-isobutoxy-2-isopropylbenzene.

The invention also provides processes and novel intermediates that are useful for preparing a compound of formulae (I), or a salt thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be pyrazinyl, pyridazine, triazine, pyridyl, or pyrimidinyl, or an N-oxide thereof.

In one specific embodiment $R^1$ is $(C_3-C_6)$alkyl or $(C_3-C_6)$cycloalkyl-$(C_1-C_3)$alkyl-.

In one specific embodiment $R^1$ is isopropyl or cyclopropylmethyl.

In one specific embodiment $R^1$ is $(C_3-C_6)$alkoxy, or $(C_3-C_6)$cycloalkyl-$(C_1-C_3)$alkoxy-.

In one specific embodiment $R^1$ is 2-methylpropoxy or cyclopropylmethoxy.

In one specific embodiment $R^2$ is $(C_3-C_6)$alkyl or $(C_3-C_6)$cycloalkyl-$(C_1-C_3)$alkyl-.

In one specific embodiment $R^2$ is isopropyl or cyclopropylmethyl.

In one specific embodiment $R^2$ is $(C_3-C_6)$alkoxy, or $(C_3-C_6)$cycloalkyl-$(C_1-C_3)$alkoxy-.

In one specific embodiment $R^2$ is 2-methylpropoxy, isopropoxy, or cyclopropylmethoxy.

In one specific embodiment $R^1$ is isopropyl, 2-methylpropoxy, or cyclopropylmethoxy.

In one specific embodiment $R^2$ is isopropyl, isopropoxy, or 2-methylpropoxy.

In one specific embodiment $R^3$ is $(C_1-C_3)$alkyl.

In one specific embodiment $R^3$ is ethyl.

In one specific embodiment $R^4$ is selected from:

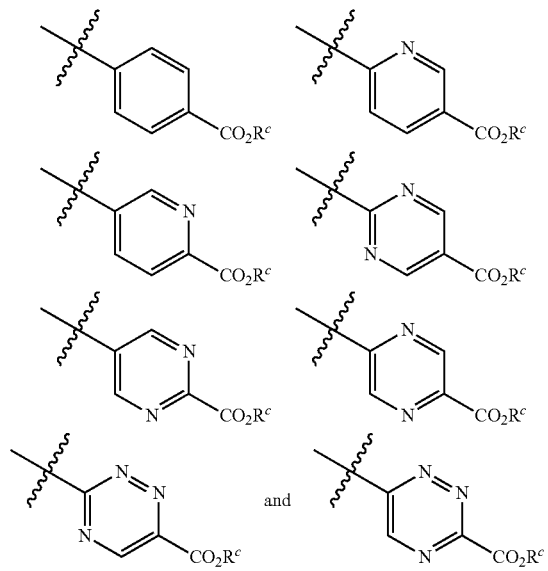

In one specific embodiment $R^4$ is selected from:

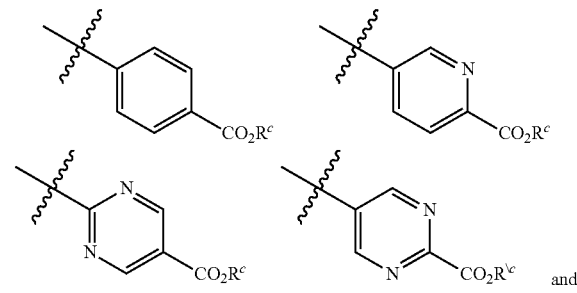

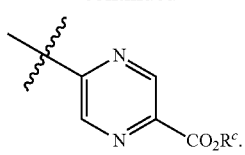
In one specific embodiment the compound is selected from the group consisting of:
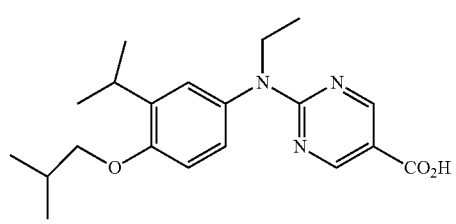
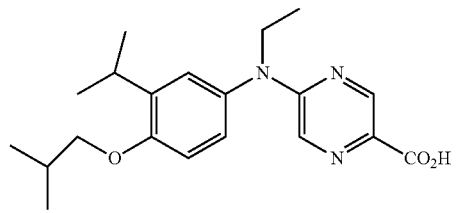
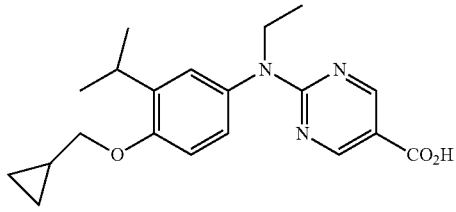
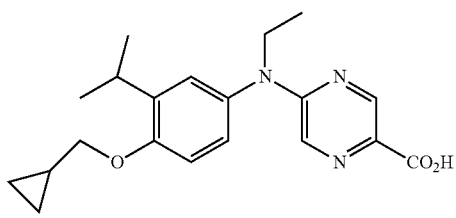
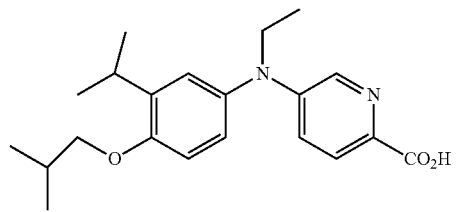
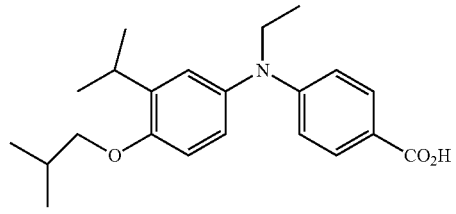
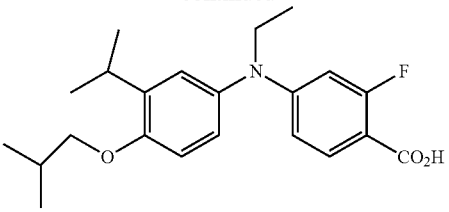
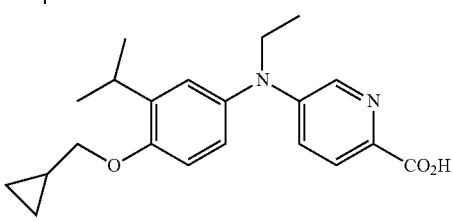
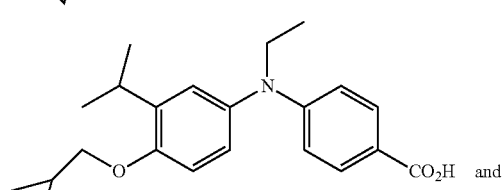
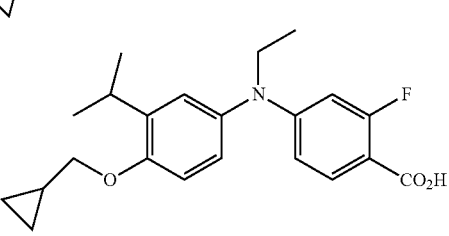
and salts thereof.
In one specific embodiment the compound is selected from the group consisting of:
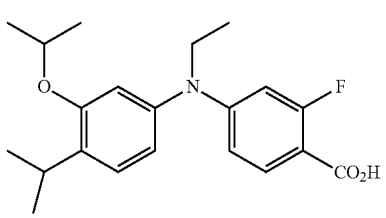
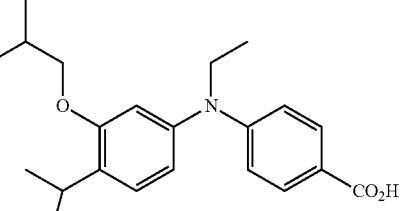
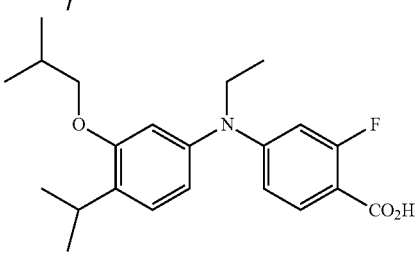

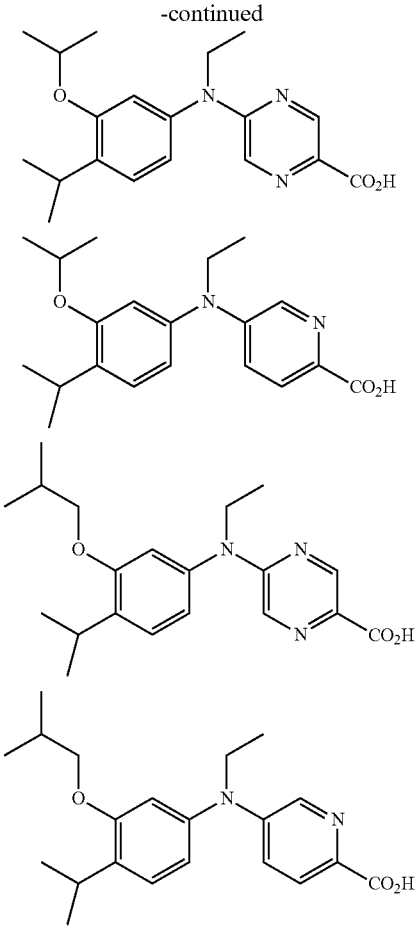

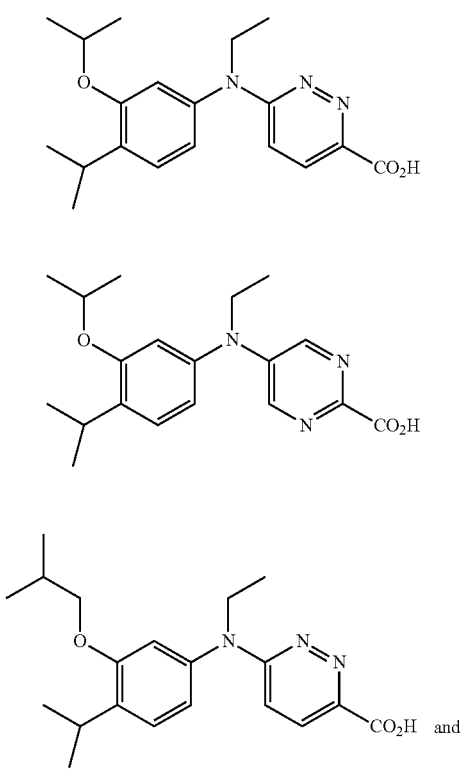 and

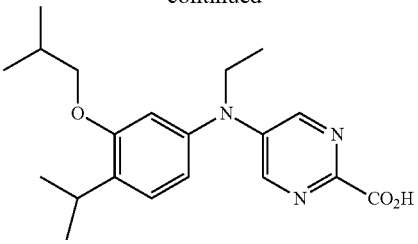

and salts thereof.

In one embodiment, the compound is not a compound of formula III:

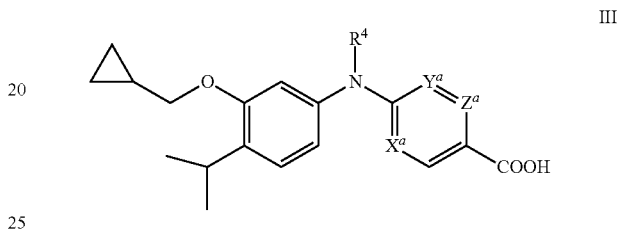

wherein:
$X^a$ is CH, $Y^a$ is CH and $Z^a$ is CH;
$X^a$ is CH, $Y^a$ is CH and $Z^a$ is N;
$X^a$ is N, $Y^a$ is N and $Z^a$ is CH; and
$R^4$ is ethyl that is optionally substituted with one or more groups independently selected from F, Cl, and Br; wherein the ring containing $X^a$, $Y^a$, and $Z^a$ is optionally substituted on carbon with one or more groups independently selected from halo;

In one embodiment, the compound is not a compound of formula IIIa, IIIb, or IIIc:

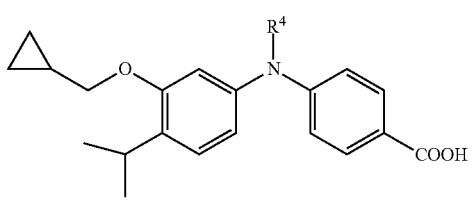

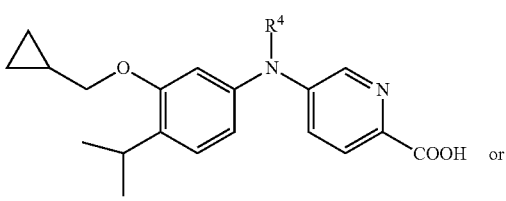

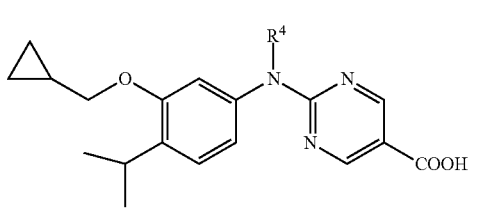

wherein:
$R^4$ is ethyl that is optionally substituted with one or more groups independently selected from F, Cl, and Br;
or a salt thereof.

In one embodiment, the compound is not a compound selected from:

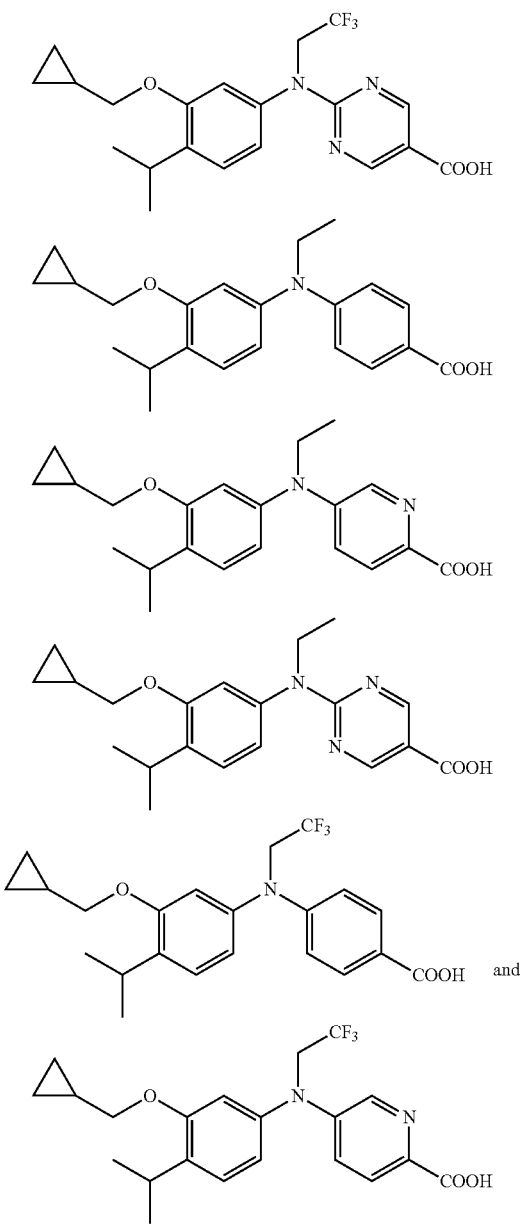

and salts thereof.

Diseases and Condition

Compounds of the invention possessing RXR agonist properties are useful for treating Alzheimer's disease. The compounds of the invention may also treat Alzheimer's disease by targeting a combination of RXR:LXR controlled genes (like ApoE), or by binding to amyloid beta oligomers (where cholesterol usually binds) and disrupting calcium channel formation in neurons (Fantini, J. et al. *ACS Chem. Neurosci.* 2014, DOI: 10.1021/cn400183w).

Compounds of the invention are also useful for treating cancers, including but not limited to, colon, breast, lung, pancreatic, skin, cutaneous T-cell lymphoma, acute promyelocytic leukemia, ovarian, bladder, kidney, head and neck cancers, and Kaposi's sarcoma. See breast cancer: Esteva, F. J. et al. *JCO*, 2003, 21, 999-1006; advanced non-small lung cancer: (a) Khuri, F. R. et al. *JCO*, 2001, 19, 2626-2637 and (b) Lamph, W. W. et al. *Clin. Cancer Res.* 2004, 10, 8656-8664; pancreatic cancer: Liby, K. *Cancer Prev. Res.* 2010, 3, 1427-1434; and colon cancer: Cesario, R. M. et al. *Cancer Letters* 2006, 240, 225-233.

Compounds of the invention possessing RXR agonist properties and/or that target the Nurr1 receptor are useful for treating Parkinson's disease (see McFarland, K., et al, *ACS Chem. Neurosci.*, 2013, 4(11), 1430-1438), while compounds of the invention possessing RXR agonist properties and/or PPARg activity may be useful for treating diabetes (see Mukherjee, R. et al. *Nature*, 1997, 386, 407-410).

The compounds of the invention may also be useful for treating, psychotic disorders such as schizophrenia. Such treatment may also be carried out in combination with other antipsychotic treatments (see Lerner, V. et al. *Clin. Neuropharmacol.* 2008, 31, 25-33).

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames *Salmonella*/microsome mutagenicity assay." Mutat. Res. 2000, 455, 29-60).

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents. In certain embodiments, compounds of the invention can be administered in combination with agents that are useful for the treatment of diseases associated with dopamine deficiency. For example, the compounds can be administered (and/or formulated) with clozapine, olanzapine, haloperidol, risperidone, perphenazine, quetiapine, or chlorpromazine.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A. RXR Selective Agonist Assay (Mammalian Two-Hybrid Assay).

Compounds are tested for RXR selective agonist activity via a mammalian two-hybrid assay in human colon cancer cells, HCT-116. The cell line is transfected with pCM-VhRXR binding domain vector (BD), hRXR activation domain (AD), pFR-Luc reporter gene containing BD-binding sites, and a *renilla* control plasmid. Cells are transfected for 18 hours utilizing a liposome-mediated transfection protocol then exposed to either the ethanol vehicle or $10^{-7}$ M Bexarotene or the indicted analog. After 24 hours the cells are lysed and a luciferase assay was completed. Analog dependent RXR binding and homodimerization, as measured by luciferase output, is compared to the parent compound Bexarotene.

Test B. RXR Agonist Assay (RXRE-Luciferase Based Assay).

An RXRE-luciferase assay is run at 25 nM in HCT-116 cells. The RXRE assays are completed using HCT-116 cells plated at 100,000 cells/well in 24 well plates. The cells are co-transfected using 250 ng of a RXRE-luciferase reporter plasmid (RXRE from the naturally occurring responsive element in the rat cellular retinol binding protein II gene), 50 ng of pSG5-human RXRα vector, 20 ng of the *renilla* control plasmid and 2 μL/well of Polyjet transfection reagent for liposome-mediated delivery of the DNA. The cells are treated with ethanol or analogs (final concentration of 25 nM) for 24-hours post-transfection. After a 24-hour incubation period, the amount of rexinoid activity is measured using luciferase output via a dual-luciferase reporter assay system according to the manufacturer's protocol (Promega, Madison, Wis.) in a Sirus luminometer (Berthold Detection System, Pforzheim, Germany). Two independent assays are conducted with four samples for each treatment group.

The invention will now be illustrated by the following non-limiting Examples.

EXAMPLES

Example 1 Synthesis of Representative Compounds of Formula (I)

As depicted below, compounds can be prepared according to the following general Scheme. It will be appreciated that, although the general method depicts the synthesis of certain compounds of the present invention, the general methods, and other methods known to one of ordinary skill in the art, can be applied to compounds and subclasses and species of the compounds described herein.

Similar to the reported synthesis for NEt-41B (*J. Med. Chem.* 2015, 58, 912-926), compound 7 can be synthesized as follows (Scheme 1):

nated with sodium hydride and then treated with ethyl iodide to give methyl ester 6 which is then saponified to give compound 7.

Example 2 Synthesis of Net-41B

While the published synthetic route to NEt-41B begins with the nitration of 2-isopropyl phenol in the presence of zinc (II) chloride under ultrasonication conditions, the route that was undertaken in the current study begins with the alkylation of 2-isopropyl phenol (33) to give 1-isobutoxy-2-isopropylbenzene (34) in 50% yield followed by nitration with concentrated (>90%) nitric acid and sulfuric acid in ethyl acetate at 0° C. to give a 3:1 mixture of mono-nitrated products 35 and 36.

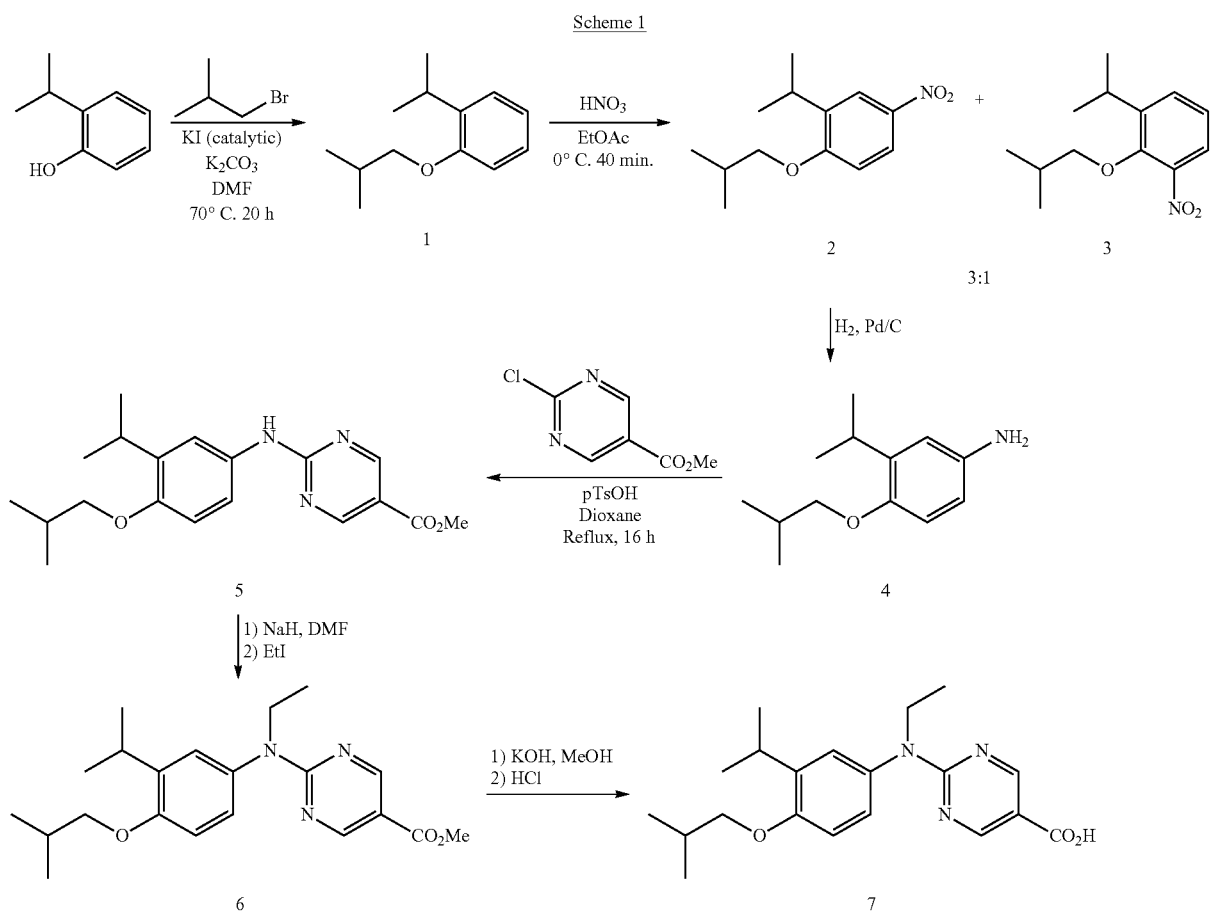

Scheme 1

Commercially available 2-isopropylphenol is converted to 1-isobutoxy-2-isoproylbenzene (1) by treatment with isobutyl bromide and potassium carbonate, with catalytic potassium iodide, in DMF at 70° C. for 20 h. Compound 1 is converted to a 3:1 mixture of 2 and 3 by treatment with concentrated (>90%) nitric acid at 0° C. in ethyl acetate. Compound 2 is reduced with hydrogen and Pd/C to give 4 which serves as the nucleophile in the NAS reaction with commercially available methyl 2-chloropyrimidine-5-carboxylate to give 5 as the product. Compound 5 is deproto-

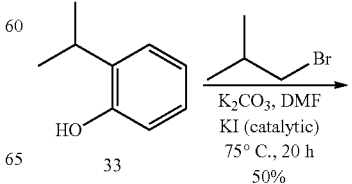

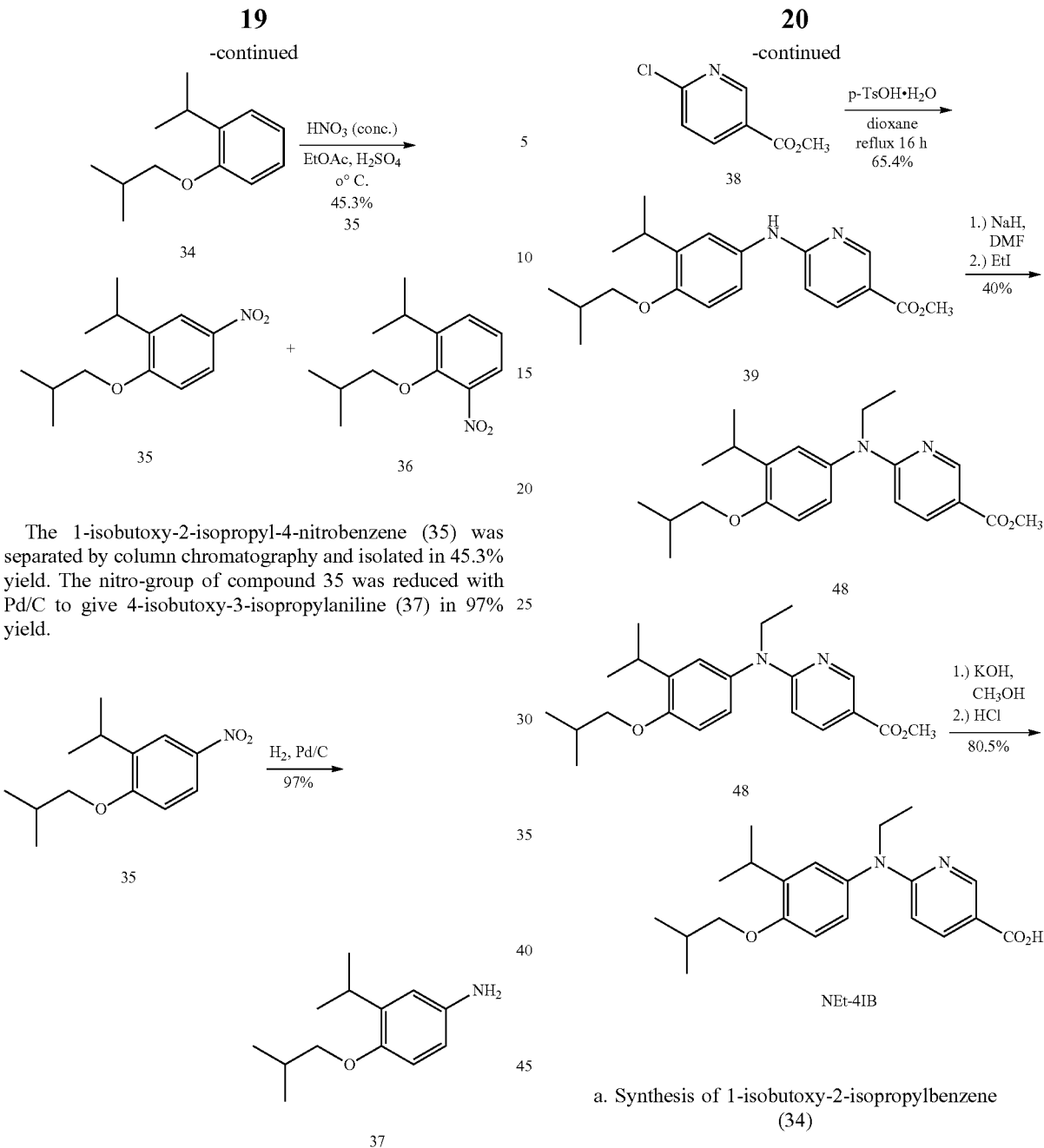

The 1-isobutoxy-2-isopropyl-4-nitrobenzene (35) was separated by column chromatography and isolated in 45.3% yield. The nitro-group of compound 35 was reduced with Pd/C to give 4-isobutoxy-3-isopropylaniline (37) in 97% yield.

Aniline 37 was combined with methyl 6-chloronicotinate (38) and para-toluene sulfonic acid in dioxane and the reaction was refluxed for 16 hours to give methyl 6-((4-isobutoxy-3-isopropylphenyl)-amino)nicotinate (39) in 65.4% yield.

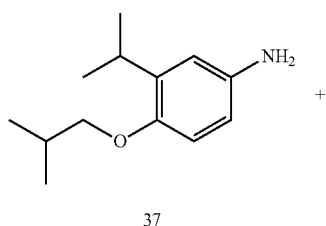

a. Synthesis of 1-isobutoxy-2-isopropylbenzene (34)

To a solution of 2-isopropylphenol (12.5 mL, 92.9 mmols) and 1-bromo-2-methylpropane (20.5 mL, 189 mmols) in DMF (50 mL) was added finely ground potassium carbonate (13.9 g, 101 mmols) and potassium iodide (0.652 g, 3.9 mmols), and the reaction was stirred for 20 h at 70-75° C. The reaction solution was then poured into water and extracted with ethyl acetate. The organic layers were washed with brine, dried over sodium sulfate and concentrated in vacuo to provide a crude oil that was purified by column chromatography (1% ethyl acetate in hexanes) to give 34 as a colorless oil (8.7947 g, 50%): $^1$H NMR (400 MHz, CDCl$_3$) δ 7.23 (d, J=7.6, 1H), 7.16 (td, J=8.0, 2.4, 1H), 6.93 (t, J=7.6, 1H), 6.85 (d, J=8.0, 1H), 3.76 (d, J=6.4, 2H), 3.39 (hept, J=6.8, 1H), 2.15 (nonet, J=6.8, 1H), 1.27 (d, J=6.8, 6H), 1.08 (d, J=6.4, 6H); $^{13}$C NMR (100.6 MHz, CDCl$_3$) δ156.3, 136.9, 126.4, 125.9, 120.2, 74.2, 28.5, 26.9, 22.6, 19.4; IR (neat) 2959, 1599, 1491, 1236 cm$^{-1}$; GC-MS-CI (M+NH$_4$)+ calcd for C$_{13}$H$_{24}$NO 210.1858, found 210.1850.

b. Synthesis of 1-isobutoxy-2-isopropyl-4-nitrobenzene (35)

To a solution of 1-isobutoxy-2-isopropylbenzene (34) (17.208 g, 89.486 mmols) in ethyl acetate (100 mL) at 0° C. was added concentrated (>90%) nitric acid (50.5 mL, 1.2 mols). The reaction was stirred at 0° C. for 40 min at which point it was carefully poured into water and extracted with ethyl acetate. The organic layer was washed with brine, dried over sodium sulfate, to give a crude oil that consisted of 35 and 36 in a 3:1 ratio—TLC separates these isomers after 4 elutions in 1% ethyl acetate:hexanes (36 $R_f$~0.5 and 35 $R_f$~0.45). This crude oil was purified by column chromatography (0.7% to 1% to 5% ethyl acetate in hexanes) to give 35 (9.6225 g, 45.3%) as a pale yellow oil: $^1$H NMR (400 MHz, CDCl$_3$) δ 8.09 (d, J=2.4, 1H), 8.06 (dd, J=8.8, 2.8, 1H), 6.84 (d, J=9.2, 1H), 3.83 (d, J=6.4, 2H), 3.35 (kept, J=6.8, 1H), 2.16 (nonet, J=6.8, 1H), 1.25 (d, J=6.8, 6H), 1.07 (d, J=6.8, 6H); $^{13}$C NMR (100.6 MHz, CDCl$_3$) 8161.5, 141.2, 138.0, 123.3, 121.9, 110.2, 28.3, 27.0, 22.1, 19.2; IR (neat) 2962, 1588, 1512, 1336, 1251 cm$^{-1}$; ES-MS (M+Na)+ calcd for C$_{13}$H$_{19}$NO$_3$Na, 260.1263, found 260.1256.

c. Synthesis of Methyl 6-((4-isobutoxy-3-isopropylphenyl)amino)nicotinate (39)

A solution of 1-isobutoxy-2-isopropyl-4-nitrobenzene (35) (2.0064 g, 8.455 mmols) in ethyl acetate (183 mL) was passed through a 10% Pd/C cartridge at 1.0 mL/minute in the ThalesNano H-Cube® at 65° C. and 2-5 bar pressure. The resulting solution was concentrated in vacuo to give 4-isobutoxy-3-isopropylaniline (37) (1.7057 g, 97%) as a yellow oil that was used without further purification: $^1$H NMR (400 MHz, CDCl$_3$) δ 6.66 (d, J=8.4, 1H), 6.63 (d, J=2.8, 1H), 6.50 (dd, J=8.4, 2.8, 1H), 3.64 (d, J=6.4, 2H), 3.63 (br s, 1H), 3.31 (hept, J=6.8, 1H), 2.09 (nonet, J=6.8, 1H), 1.20 (d, J=6.8, 6H), 1.03 (d, J=6.8, 6H); $^{13}$C NMR (100.6 MHz, CDCl$_3$) δ 149.8, 138.9, 138.2, 114.3, 113.1, 112.6, 75.2, 28.5, 26.8, 22.6, 19.4. To a solution of 37 (1.783 g, 8.60 mmols) and methyl 6-chloronicotinate (1.6567 g, 9.655 mmols) in dioxane (15.0 mL) was added para-toluenesulfonic acid monohydrate (1.7977 g, 9.45 mmols) and the reaction was refluxed overnight in an oil bath at 111° C. The reaction was cooled to room temperature, and then the mixture was poured into water, extracted with ethyl acetate, and the organic layers were washed with brine, dried over sodium sulfate and concentrated to give a crude oil that was purified by column chromatography (150 mL SiO$_2$, 6% ethyl acetate:hexanes) to give 39 (1.9259 g, 65.4%) as a white crystalline solid, m.p. 123-124° C.: $^1$H NMR (400 MHz, CDCl$_3$) δ 8.76 (dd, J=2.4, 0.8, 1H), 8.00 (dd, J=8.8, 2.4, 1H), 7.77 (br s, 1H), 7.11 (s, 1H), 7.09 (dd, J=7.6, 2.8, 1H), 6.82 (dd, J=7.6, 0.8, 1H), 6.65 (dd, J=8.8, 0.8, 1H), 3.86 (s, 3H), 3.74 (d, J=6.0, 2H), 3.36 (hept, J=6.8, 1H), 2.13 (nonet, J=6.8, 1H), 1.22 (d, J=6.8, 6H), 1.06 (d, J=6.8, 6H); $^{13}$C NMR (100.6 MHz, CDCl$_3$) δ 166.1, 160.1, 154.1, 151.1, 138.9, 138.4, 131.0, 122.2, 121.9, 115.9, 111.6, 105.5, 51.6, 28.4, 26.9, 22.5, 19.3; IR (neat) 3235, 2953, 1721, 1612, 1598, 1496, 1277, 1115 cm$^{-1}$; ES-MS (M+H)+ calcd for C$_{20}$H$_{27}$H$_2$O$_3$ 343.2022, found 343.2024.

d. Synthesis of methyl 6-(ethyl(4-isobutoxy-3-isopropylphenyl)amino)nicotinate (48)

To a flame-dried, 100 mL round-bottomed flask equipped with a magnetic stir bar was added a 60% dispersion of sodium hydride in mineral oil (0.2351 g, 5.88 mmol). The dispersion of sodium hydride was washed with hexanes (3 mL, twice) and dried under vacuum and suspended in 3.0 mL of DMF under nitrogen. To this solution of sodium hydride in DMF was added a solution of 39 (0.8331 g, 2.433 mmol) in DMF (9.2 mL), and the reaction was stirred for 15 min., and then ethyl iodide (0.30 mL, 3.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 48 (0.3629 g, 40%) as a colorless oil: $^1$H NMR (400 MHz, CDCl$_3$) δ 8.83 (dd, J=2.0, 0.4, 1H), 7.77 (dd, J=8.8, 2.4, 1H), 7.01 (d, J=2.4, 1H), 6.96 (dd, J=8.4, 2.4, 1H), 6.86 (d, J=8.4, 1H), 6.14 (dd, J=8.8, 0.4, 1H), 4.00 (q, J=7.2, 211), 3.85 (s, 3H), 3.76 (d, J=6.4, 2H), 3.36 (hept, J=6.8, 1H), 2.14 (nonet, J=6.8, 1H), 1.21 (t, J=7.2, 3H), 1.20 (d, J=6.8, 6H), 1.08 (d, J=6.8, 6H); $^{13}$C NMR (100.6 MHz, CDCl$_3$) δ 165.3, 162.8, 159.7, 155.1, 138.1, 135.3, 125.4, 125.3, 112.7, 111.2, 74.2, 51.6, 46.4, 28.4, 27.1, 22.4, 19.4, 12.7; IR (neat) 2959, 1711, 1596, 1495, 1263 cm$^{-1}$; ES-MS (M)+ calcd for C$_{22}$H$_{30}$N$_2$O$_3$ 370.2256, found 370.2242.

e. Synthesis of 6-(ethyl(4-isobutoxy-3-isopropylphenyl)amino)nicotinic acid (NEt-41B)

To a solution of 48 (0.9265 g, 2.501 mmols) in methanol (9.0 mL) was added a solution of KOH (0.4545 g, 8.100 mmols) in water (0.56 mL) and the solution was heated to reflux with stirring for 1 hour. The solution was then cooled to room temperature, quenched with IN HCl (80 mL), extracted with ethyl acetate, the organic layer was washed with brine, dried over sodium sulfate, filtered and concentrated in vacuo to give a crude product that was purified by column chromatography (25 mL SiO$_2$, 20%-52% ethyl acetate:hexanes) to give NEt-41B (0.7184 g, 80.5%) as a crystalline solid, m.p. 158.5-168.2° C.: $^1$H NMR (400 MHz, CDCl$_3$) 610.90 (br s, 1H), 8.92 (d, J=2.4, 1H), 7.82 (dd, J=9.2, 2.4, 1H), 7.03 (d, J=2.4, 1H), 6.98 (dd, J=8.4, 2.4, 1H), 6.87 (d, J=8.4, 1H), 6.17 (d, J=9.2, 1H), 4.03 (q, J=7.2, 2H), 3.77 (d, J=6.4, 2H), 3.36 (hept, J=6.8, 1H), 2.15 (nonet, J=6.4, 1H), 1.24 (t, J=7.2, 3H), 1.22 (d, J=7.2, 6H), 1.08 (d, J=6.4, 6H); $^{13}$C NMR (100.6 MHz, CDCl$_3$) δ 171.4, 160.9, 155.4, 151.6, 139.1, 137.9, 135.6, 126.0, 125.9, 113.3, 111.9, 107.5, 74.4, 45.6, 28.4, 27.0, 22.5, 19.3, 12.9; IR (neat) 2959, 1661, 1592, 1495, 1271, 785 cm$^{-1}$; ES-MS (M−H)− calcd for C$_{21}$H$_{27}$N$_2$O$_3$ 355.2022, found 355.2022. Anal. Calcd for C$_{21}$H$_{28}$N$_2$O$_3$: C, 70.76; H, 7.92; N, 7.86. Found: C, 70.86; H, 7.72; N, 7.85.

Example 3 Synthesis of Compound 7

Aniline 37 was combined with methyl 2-chloropyrimidine-5-carboxylate (40) and para-toluene sulfonic acid in dioxane and the reaction was refluxed for 16 hours to give methyl 2-((4-isobutoxy-3-isopropylphenyl)amino)pyrimidine-5-carboxylate (41) in 77.2% yield

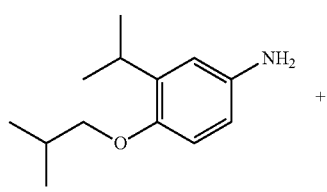

37

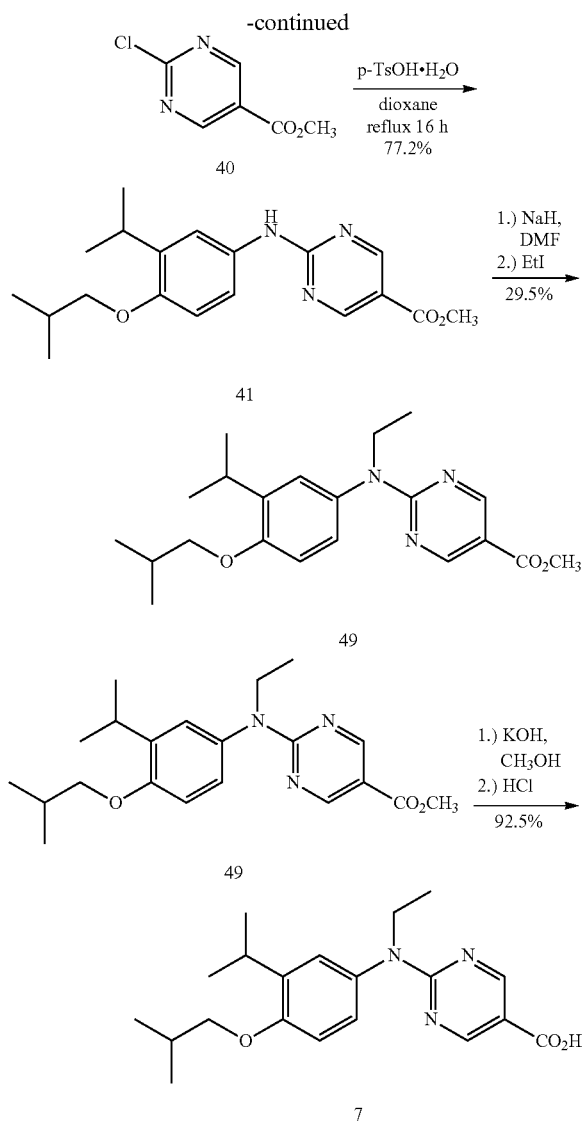

a. Synthesis of methyl 2-((4-isobutoxy-3-isopropylphenyl)amino)pyrimidine-5-carboxylate (41)

To a solution of 37 (1.7057 g, 8.23 mmols) and methyl 2-chloropyrimidine-5-carboxylate (1.5852 g, 9.1859 mmols) in dioxane (15.0 mL) was added para-toluenesulfonic acid monohydrate (1.7197 g, 9.04 mmols) and the reaction was refluxed overnight in an oil bath at 111° C. The reaction was cooled to room temperature, and then the mixture was poured into water, extracted with ethyl acetate, and the organic layers were washed with brine, dried over sodium sulfate and concentrated to give a crude oil that was purified by column chromatography (150 mL SiO$_2$, 10% ethyl acetate:hexanes) to give 41 (2.1821 g, 71.3%) as a white crystalline solid, m.p. 122-124.2° C.: $^1$H NMR (400 MHz, CDCl$_3$) δ 8.92 (s, 2H), 8.36 (br s, 1H), 7.44 (dd, J=8.8, 2.4, 1H), 7.27 (d, J=2.4, 1H), 6.83 (d, J=8.8, 1H), 3.89 (s, 3H), 3.74 (d, J=6.0, 2H), 3.37 (hept, J=6.8, 1H), 2.12 (nonet, J=6.8, 1H), 1.24 (d, J=6.8, 6H), 1.06 (d, J=6.4, 6H); $^{13}$C NMR (100.6 MHz, CDCl$_3$) δ 164.7, 161.7, 160.0, 153.5, 137.7, 130.4, 120.1, 120.1, 114.4, 111.3, 74.5, 51.8, 28.4, 26.9, 22.5, 19.3; IR (neat) 3261, 2956, 1721, 1597, 803 cm$^{-1}$; ES-MS (M+Na)+ calcd for C$_{29}$H$_{25}$N$_3$O$_3$Na, 366.1794, found 366.1801.

b. Synthesis of methyl 2-(ethyl(4-isobutoxy-3-isopropylphenyl)amino)pyrimidine-5-carboxylate (49)

To a flame-dried, 100 mL round-bottomed flask equipped with a magnetic stir bar was added a 60% dispersion of sodium hydride in mineral oil (0.2377 g, 5.95 mmol). The dispersion of sodium hydride was washed with hexanes (3 mL, twice) and dried under vacuum and suspended in 3.0 mL of DMF under nitrogen. To this solution of sodium hydride in DMF was added a solution of 41 (0.8442 g, 2.458 mmol) in DMF (9.2 mL), and the reaction was stirred for 15 min., and then ethyl iodide (0.30 mL, 3.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 49 (0.2698 g, 29.5%) as a white crystalline solid, m.p. 122.8-125.8° C.: $^1$H NMR (400 MHz, CDCl$_3$) δ 8.83 (br s, 2H), 7.03 (d, J=2.8, 1H), 6.99 (dd, J=8.4, 2.8, 1H), 6.85 (d, J=8.4, 1H), 4.02 (q, J=6.8, 2H), 3.86 (s, 3H), 3.75 (d, J=6.4, 2H), 3.35 (hept, J=6.8, 1H), 2.13 (nonet, J=6.8, 1H), 1.24 (t, J=6.8, 3H), 1.23 (d, J=6.8, 6H), 1.06 (d, J=6.8, 6H); $^{13}$C NMR (100.6 MHz, CDCl$_3$) δ 165.3, 162.8, 159.7, 155.1, 138.1, 135.3, 125.4, 125.3, 112.7, 111.2, 74.2, 51.6, 46.4, 28.4, 27.1, 22.4, 19.4, 12.7; IR (neat) 2960, 1708, 1595, 1494, 1284, 805 cm$^{-1}$; ES-MS (M+Na)+ calcd for C$_{21}$H$_{29}$N$_3$O$_3$Na, 394.2107, found 394.2109.

c. Synthesis of 2-(ethyl(4-isobutoxy-3-isopropylphenyl)amino)pyrimidine-5-carboxylic acid (7)

To a solution of 49 (0.7580 g, 2.04 mmols) in methanol (7.3 mL) was added a solution of KOH (0.3846 g, 6.854 mmols) in water (0.46 mL) and the solution was heated to reflux with stirring for 1 hour. The solution was then cooled to room temperature, quenched with 1N HCl (80 mL), and the resulting precipitate was filtered to give a crude product that was purified by column chromatography (25 mL SiO$_2$, 20%-60% ethyl acetate:hexanes) to give 7 (0.6753 g, 92.6%) as a crystalline solid, m.p. 201.5-202.8° C.: $^1$H NMR (400 MHz, CDCl$_3$) 610.65 (br s, 1H), 8.88 (br s, 2H), 7.03 (d, J=2.4, 1H), 7.00 (dd, J=8.4, 2.4, 1H), 6.86 (d, J=8.4, 1H), 4.05 (q, J=7.2, 2H), 3.74 (d, J=6.0, 2H), 3.35 (hept, J=6.8, 1H), 2.13 (nonet, J=6.4, 1H), 1.27 (t, J=7.2, 3H), 1.25 (d, J=6.8, 6H), 1.08 (d, J=6.8, 6H); $^{13}$C NMR (100.6 MHz, CDCl$_3$) δ 169.8, 162.7, 160.4, 155.3, 138.3, 135.0, 125.5, 125.3, 112.0, 111.3, 74.2, 46.6, 28.4, 27.1, 22.4, 19.4, 12.7; IR (neat) 2961, 1663, 1589, 1518, 1495, 1271, 807 cm$^{-1}$; ES-MS (M−H)− calcd for C$_{20}$H$_{26}$N$_3$O$_3$ 356.1974, found 356.1965. Anal. Calcd for C$_{20}$H$_{27}$N$_3$O$_3$: C, 67.20; H, 7.61; N, 11.76. Found: C, 67.26; H, 7.67; N, 11.75.

Example 4 Synthesis of Compound 12

Aniline 37 was coupled to methyl 4-iodobenzoate (44) with tris(dibenzylideneacetone)-dipalladium in the presence of rac-BINAP and cesium carbonate to give methyl 4-((4-isobutoxy-3-isopropylphenyl)amino)benzoate (45) in 54% yield

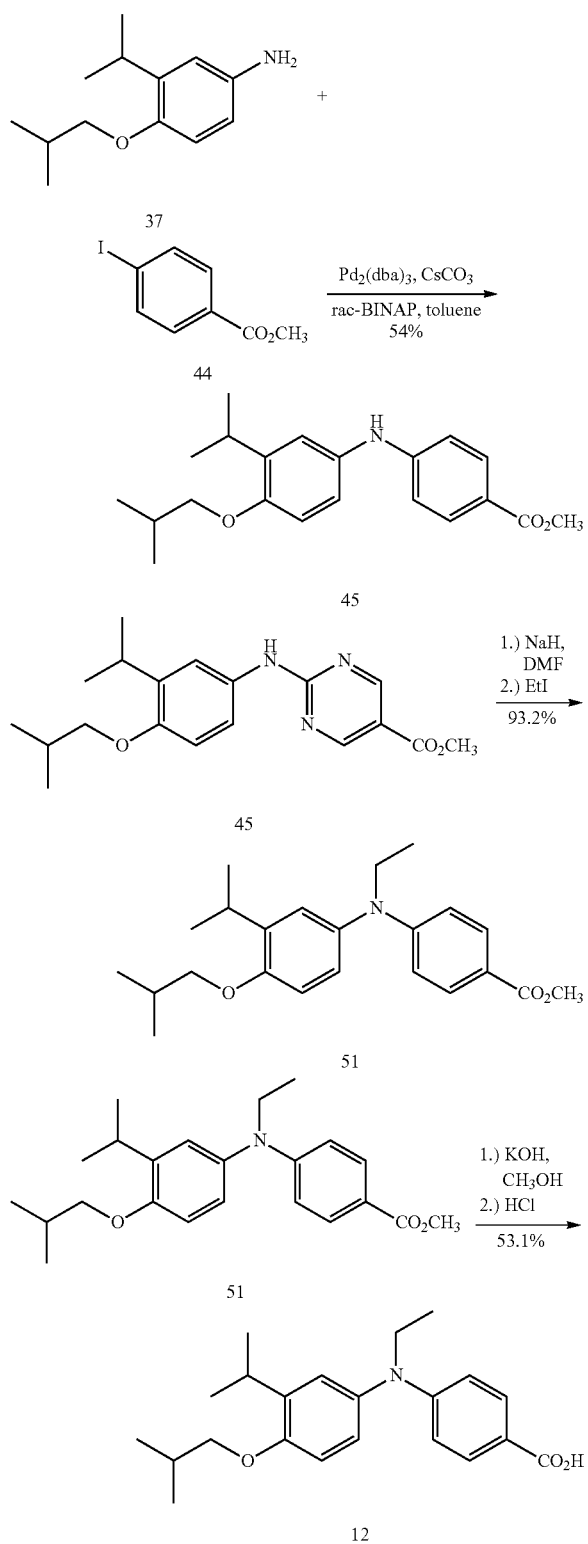

a. Synthesis of methyl 4-((4-isobutoxy-3-isopropylphenyl)amino)benzoate (45)

To a solution of 37 (1.1807 g, 5.695 mmol), methy 4-iodobenzoate 44 (1.6531 g, 6.308 mmols), CsCO₃ (4.9777 g, 15.28 mmol), rac-BINAP (0.3097 g, 0.50 mmol) in toluene (7.4 mL) in a 100 mL round-bottomed flask was added Pd₂(dba)₃ (0.2868 g, 1.64 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO₂, 6% ethyl acetate:hexanes to 12% ethyl acetate: hexanes) to give 45 (1.0494 g, 54%) as a crystalline solid, m.p. 101.1-103.8° C.: $^1$H NMR (400 MHz, CDCl₃) δ 8.13 (d, J=8.4, 1H), 7.88 (br s, 1H), 7.69 (d, J=8.4, 1H), 7.06 (d, J=8.8, 1H), 6.80 (d, J=8.4, 4H), 3.86 (s, 3H), 3.74 (d, J=6.4, 2H), 3.35 (hept, J=7.2, 1H), 2.13 (nonet, J=6.8, 1H), 1.21 (d, J=7.2, 6H), 1.06 (d, J=6.8, 6H); $^{13}$C NMR (100.6 MHz, CDCl₃) δ 167.0, 151.2, 131.5, 131.5, 131.4, 131.4, 130.8, 130.2, 129.7, 127.2, 121.4, 113.1, 74.6, 51.5, 28.5, 26.9, 22.5, 19.3; IR (neat) 3379, 2958, 1684, 1612, 1591, 1283, 1177 cm⁻¹; ES-MS (M+Na)+ calcd for C₂₁H₂₇NO₃Na, 364.1889, found 364.1896.

b. Synthesis of methyl 4-(ethyl(4-isobutoxy-3-isopropylphenyl)amino)benzoate (51)

To a flame-dried, 100 mL round-bottomed flask equipped with a magnetic stir bar was added a 60% dispersion of sodium hydride in mineral oil (0.2417 g, 6.05 mmol). The dispersion of sodium hydride was washed with hexanes (3 mL, twice) and dried under vacuum and suspended in 3.0 mL of DMF under nitrogen. To this solution of sodium hydride in DMF was added a solution of 45 (0.8581 g, 2.513 mmol) in DMF (9.2 mL), and the reaction was stirred for 15 min., and then ethyl iodide (0.30 mL, 3.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO₂, 6% ethyl acetate:hexanes) to give 51 (0.8655 g, 93.2%) as a white crystalline solid, m.p. 86.8-89.9° C.: $^1$H NMR (400 MHz, CDCl₃) δ 7.80 (dd, J=7.2, 2.4, 1H), 7.01 (d, J=2.8, 1H), 6.95 (dd, J=8.4, 2.4, 1H), 6.84 (d, J=8.4, 1H), 6.58 (dd, J=7.2, 2.0, 1H), 3.84 (s, 3H), 3.76 (d, J=6.0, 2H), 3.71 (q, J=7.2, 2H), 3.35 (hept, J=7.2, 1H), 2.14 (nonet, J=6.8, 1H), 1.24 (t, J=6.8, 3H), 1.21 (d, J=7.2, 6H), 1.08 (d, J=6.8, 6H); $^{13}$C NMR (100.6 MHz, CDCl₃) δ 167.3, 154.7, 152.2, 138.8, 137.9, 131.0, 126.0, 125.9, 117.3, 112.0, 111.8, 74.4, 51.4, 46.7, 28.5, 27.0, 22.5, 19.4, 12.3; IR (neat) 2958, 1698, 1609, 1598, 1495, 1269, 1179, 767 cm⁻¹; ES-MS (M)+ calcd for C₂₃H₃₁NO₃Na, 392.2202, found 392.2196.

c. Synthesis of 4-(ethyl(4-isobutoxy-3-isopropylphenyl)amino)benzoic acid (12)

To a solution of 51 (0.7035 g, 1.904 mmols) in methanol (6.8 mL) was added a solution of KOH (0.3626 g, 6.462 mmols) in water (0.43 mL) and the solution was heated to reflux with stirring for 1 hour. The solution was then cooled to room temperature, quenched with 1N HCl (80 mL), and the resulting precipitate was filtered to give a crude product that was purified by column chromatography (25 mL SiO₂, 10%-60% ethyl acetate:hexanes) to give 12 (0.3594 g, 53.1%) as a crystalline solid, m.p. 179.4-181.0° C.: $^1$H NMR (400 MHz, CDCl$_3$) δ10.89 (br s, 1H), 7.88 (d, J=8.8, 2H), 7.03 (d, J=2.8, 1H), 6.97 (dd, J=8.8, 2.8, 1H), 6.86 (d, J=8.4, 1H), 6.60 (d, J=9.2, 2H), 3.77 (d, J=6.4, 2H), 3.75 (q, J=7.2, 2H), 3.36 (hept, J=6.8, 1H), 2.15 (nonet, J=6.8, 1H), 1.25 (t, J=7.2, 3H), 1.23 (d, J=7.2, 6H), 1.09 (d, J=6.8, 6H); $^{13}$C NMR (100.6 MHz, CDCl$_3$) δ 172.4, 154.8, 152.9, 138.9, 137.7, 131.8, 126.0, 116.3, 112.0, 111.8, 74.4, 46.8, 28.5, 27.0, 22.5, 19.4, 12.3; IR (neat) 2955, 1664, 1593, 1268, 1273, 1181, 773 cm$^{-1}$; ES-MS (M–H)– calcd for C$_{22}$H$_{28}$NO$_3$ 354.2069, found 354.2077. Anal. Calcd for C$_{22}$H$_{29}$NO$_3$: C, 74.33; H, 8.22; N, 3.94. Found: C, 74.42; H, 8.34; N, 3.92.

Example 5 Synthesis of Compound 13

Aniline 37 was coupled to methyl 2-fluoro-4-iodobenzoate (42) with tris(dibenzylideneacetone)-dipalladium in the presence of rac-BINAP and cesium carbonate to give methyl 2-fluoro-4-((4-isobutoxy-3-isopropylphenyl)amino)benzoate (43) in 92% yield.

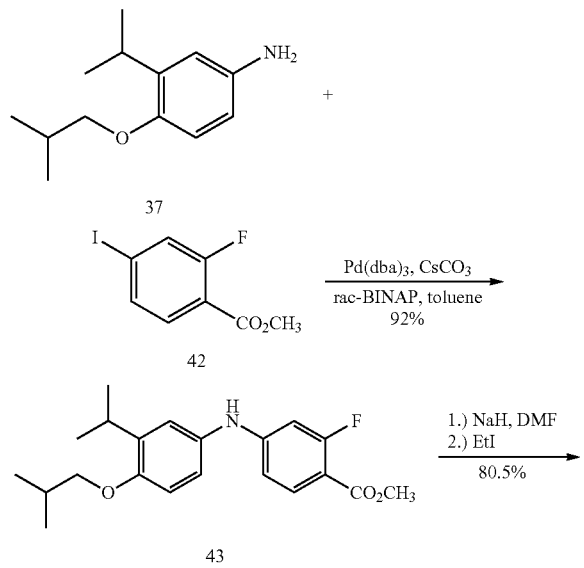

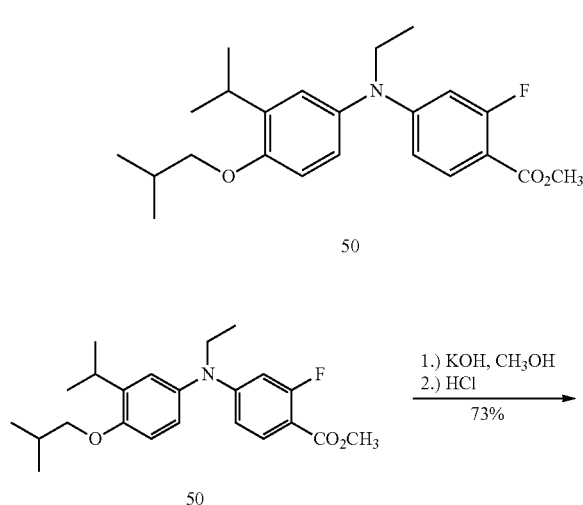

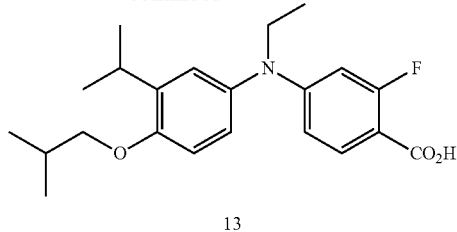

a. Synthesis of methyl 2-fluoro-4-((4-isobutoxy-3-isopropylphenyl)amino)benzoate (43)

To a solution of 37 (1.3452 g, 6.49 mmol), methy 2-fluoro-4-iodobenzoate 42 (1.9807 g, 7.07 mmols), CsCO$_3$ (5.5562 g, 17.08 mmol), rac-BINAP (0.3386 g, 0.55 mmol) in toluene (8.6 mL) in a 100 mL round-bottomed flask was added Pd$_2$(dba)$_3$ (0.319 g, 1.82 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO$_2$, 6% ethyl acetate:hexanes to 12% ethyl acetate: hexanes) to give 43 (2.147 g, 88.9%) as a crystalline solid, m.p. 93.4-100.9° C.: $^1$H NMR (400 MHz, CDCl$_3$) δ 7.84-7.75 (m, 1H), 7.01 (br s, 1H), 6.97-6.72 (m, 1H), 6.80 (d, J=8.4, 1 H), 6.54 (d, J=8.4, 1H), 6.47 (d, J=13.6, 1H), 3.86 (s, 3H), 3.75 (d, J=6.0, 2H), 3.35 (hept, J=6.8, 1H), 2.13 (nonet, J=6.8, 1H), 1.21 (d, J=6.8, 6H), 1.06 (d, J=6.8, 6H); $^{13}$C NMR (100.6 MHz, CDCl$_3$) δ 165.3, 164.9, 164.9, 164.5, 164.4, 164.2, 161.6, 155.2, 153.9, 152.0, 151.9, 139.4, 138.5, 136.9, 133.6, 133.0, 131.9, 128.9, 128.3, 125.7, 125.5, 122.1, 121.7, 116.9, 112.1, 112.0, 111.9, 111.7, 109.7, 109.4, 109.3, 107.4, 107.3, 100.6, 100.3, 74.6, 51.6, 28.4, 26.9, 22.5, 22.4, 19.3; IR (neat) 3343, 2960, 1686, 1618, 1603, 1498, 1439 cm$^{-1}$; ES-MS (M+Na)+ calcd for C$_{21}$H$_{26}$NFO$_3$Na, 382.1794, found 382.1795.

b. Synthesis of methyl 4-(ethyl(4-isobutoxy-3-isopropylphenyl)amino)-2-fluorobenzoate (50)

To a flame-dried, 100 mL round-bottomed flask equipped with a magnetic stir bar was added a 60% dispersion of sodium hydride in mineral oil (0.2461 g, 6.16 mmol). The dispersion of sodium hydride was washed with hexanes (3 mL, twice) and dried under vacuum and suspended in 3.0 mL of DMF under nitrogen. To this solution of sodium hydride in DMF was added a solution of 43 (0.8918 g, 2.301 mmol) in DMF (9.2 mL), and the reaction was stirred for 15 min., and then ethyl iodide (0.30 mL, 3.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 50 (0.7741 g, 80.5%) as a white crystalline solid, m.p. 66-71° C.: $^1$H NMR (400 MHz, CDCl$_3$) δ 7.70 (t, J=8.8, 1H), 6.98 (d, J=2.4, 1H), 6.93 (dd, J=8.8, 2.4, 1H), 6.84 (d, J=8.8, 1H), 6.32 (dd, J=8.8, 2.4, 1H), 6.22 (dd, J=15.2, 2.4, 1H), 3.85 (s, 3H), 3.76 (d, J=6.0, 2H), 3.69 (q, J=7.2, 2H), 3.35 (hept, J=6.8, 1H), 2.14 (nonet, J=6.8, 1H), 1.22 (t, J=7.2, 3H), 1.22 (d, J=6.8, 6H), 1.08 (d, J=6.4, 6H); $^{13}$C NMR (100.6 MHz, CDCl$_3$) δ 165.1, 165.1, 162.6, 155.0, 154.1, 154.0, 139.0, 137.2, 133.1, 133.0, 126.0, 125.9, 111.9, 108.1, 105.2, 105.1, 99.8, 99.6, 74.4, 51.5, 46.9, 28.5, 27.0, 22.5, 19.4, 12.2; IR (neat) 2957, 1707, 1692, 1620, 1495, 1299, 763 cm$^{-1}$; ES-MS (M)+ calcd for C$_{23}$H$_{30}$FNO$_3$ 387.2210, found 387.2200.

c. Synthesis of 4-(ethyl(4-isobutoxy-3-isopropyl-phenyl)amino)-2-fluorobenzoic acid (13)

To a solution of 50 (0.6837 g, 1.764 mmols) in methanol (6.0 mL) was added a solution of KOH (0.3493 g, 6.225 mmols) in water (0.41 mL) and the solution was heated to reflux with stirring for 1 hour. The solution was then cooled to room temperature, quenched with 1N HCl (80 mL), and the resulting precipitate was filtered to give a crude product that was purified by column chromatography (25 mL SiO$_2$, 10%-60% ethyl acetate:hexanes) to give 13 (0.4821 g, 73%) as a crystalline solid, m.p. 184-186° C.: $^1$H NMR (400 MHz, CDCl$_3$) δ10.01 (br s, 1H), 7.77 (t, J=9.2, 1H), 6.99 (d, J=2.4, 1H), 6.94 (dd, J=8.4, 2.4, 1H), 6.85 (d, J=8.8, 1H), 6.34 (d, J=2.4, 1H), 6.32 (d, J=2.4, 1H), 3.76 (d, J=6.4, 2H), 3.70 (q, J=7.2, 2H), 3.74 (d, J=7.2, 2H), 3.35 (hept, J=6.8, 1H), 2.15 (nonet, J=6.8, 1H), 1.24 (t, J=7.2, 3H), 1.22 (d, J=6.8, 6H), 1.08 (d, J=6.8, 6H); $^{13}$C NMR (100.6 MHz, CDCl$_3$) δ 169.7, 165.8, 163.3, 155.2, 154.8, 154.7, 139.1, 137.0, 133.7, 126.0, 125.9, 111.9, 108.1, 104.1, 104.0, 99.8, 99.5, 74.4, 47.0, 28.4, 27.0, 22.5, 19.3, 12.2; IR (neat) 2958, 1667, 1613, 1600, 1496, 1299, 1273, 1244, 836 cm$^{-1}$; ES-MS (M-H)- calcd for C$_{22}$H$_{27}$FNO$_3$ 372.1975, found 372.1982. Anal. Calcd for C$_{22}$H$_{28}$FNO$_3$: C, 70.75; H, 7.56; N, 3.75; F, 5.09. Found: C, 70.83; H, 7.69; N, 3.71; F, 4.58.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from the group consisting of:

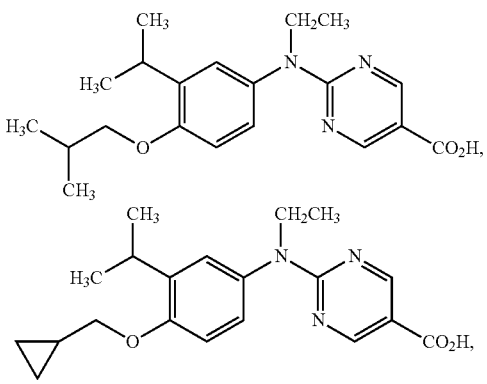

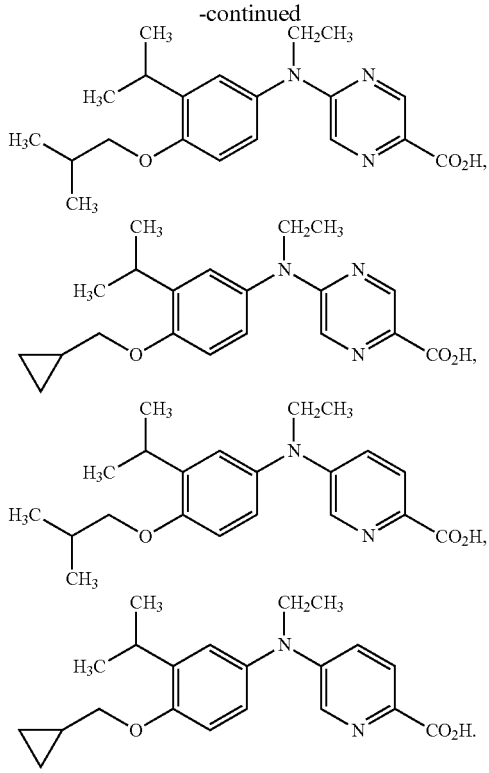

or a pharmaceutically acceptable salt thereof.

2. A pharmaceutical composition comprising a compound of claim 1, or a pharmaceutically acceptable salt thereof, and a pharmaceutically acceptable carrier.

3. A method for treating Alzheimer's disease, Parkinson's disease, diabetes, cancer or a psychotic disorder in an animal, comprising administering to the animal a compound of claim 1, or a pharmaceutically acceptable salt thereof.

4. A method for treating diabetes in an animal, comprising administering to the animal a compound of claim 1, or a pharmaceutically acceptable salt thereof.

5. A method for treating cancer in an animal, comprising administering to the animal a compound of claim 1, or a pharmaceutically acceptable salt thereof.

6. A method for treating asthma in an animal, comprising administering to the animal a compound of claim 1, or a pharmaceutically acceptable salt thereof.

7. A method for treating an allergic condition in an animal, comprising administering to the animal a compound of claim 1, or a pharmaceutically acceptable salt thereof.

8. A method for reducing inflammation or hyperresponsiveness in an animal, comprising administering to the animal a compound of claim 1, or a pharmaceutically acceptable salt thereof.

9. A method for lowering IL-4, IL-5 or IL-6 levels in an animal, comprising administering to the animal a compound of claim 1, or a pharmaceutically acceptable salt thereof.

* * * * *